US012797533B2

(12) United States Patent
Shin et al.

(10) Patent No.: US 12,797,533 B2
(45) Date of Patent: Nov. 17, 2026

(54) BIO KIT FOR EXTRACTING BODILY FLUIDS CONTAINING STEM CELLS

(71) Applicant: Rev-Med, Inc., Seongnam-si (KR)

(72) Inventors: Bong Geun Shin, Suwon-si (KR); Cheon Seog Lee, Yongin-si (KR); Dae Kwan Kim, Namyangju-si (KR)

(73) Assignee: Rev-Med, Inc., Seongnam-si (KR)

( * ) Notice: Subject to any disclaimer, the term of this patent is extended or adjusted under 35 U.S.C. 154(b) by 941 days.

(21) Appl. No.: 17/707,089

(22) Filed: Mar. 29, 2022

(65) Prior Publication Data

US 2022/0313891 A1 Oct. 6, 2022

(30) Foreign Application Priority Data

Mar. 30, 2021 (KR) ........................ 10-2021-0041242

(51) Int. Cl.

*A61M 1/36* (2006.01)
*B04B 5/04* (2006.01)
*B04B 7/04* (2006.01)

(52) U.S. Cl.

CPC ... *A61M 1/3693* (2013.01); *A61M 2202/0415* (2013.01); *A61M 2202/0427* (2013.01);
(Continued)

(58) Field of Classification Search

CPC ........ A61M 1/3693; A61M 2202/0415; A61M 2202/0427; A61M 2206/10; A61M 1/029;
(Continued)

(56) References Cited

U.S. PATENT DOCUMENTS 5,673,988 A * 10/1997 Fujita ...................... F21S 6/002 362/159
2014/0205514 A1 7/2014 Hwang
(Continued)

FOREIGN PATENT DOCUMENTS

JP 2020-81881 A 6/2020
KR 10-1170028 B1 8/2012
(Continued)

OTHER PUBLICATIONS

"Notice of Reasons for Refusal" for JP 2022-053582 by Japan Patent Office dated Mar. 22, 2023.
(Continued)

*Primary Examiner* — Claire X Wang
*Assistant Examiner* — Shuyi S. Liu
(74) *Attorney, Agent, or Firm* — BROADVIEW IP LAW, PC

(57) ABSTRACT

The present invention may include an upper cap having an opening/closing member for opening and closing an inlet through which a blood is injected; a main body housing having an open upper end outer surface thereof assembled with the upper cap, and having an inner space in which the blood is filled with; an adjustment housing that is coupled to the main body housing to seal the open lower end of the main body housing, and is movably assembled with respect to the main body housing so that a buffy coat layer is positioned on a neck portion; and a side cap fixed to the neck portion by forming a needle hole through which an end of an injection needle for extraction enters and exits in area corresponding to a sealing member to seal an extraction hole formed through the neck portion.

2 Claims, 10 Drawing Sheets

(52) U.S. Cl.
CPC ........ *A61M 2206/10* (2013.01); *B04B 5/0414* (2013.01); *B04B 7/04* (2013.01)

(58) Field of Classification Search
CPC ........ A61M 2202/0437; A61M 1/3633; A61M 2202/0439; B04B 5/0414; B04B 7/04; B04B 7/02; B04B 7/12; B01L 2200/12; B01L 2300/048; B01L 3/5021; C12M 23/06; C12M 33/04; C12M 33/10
See application file for complete search history.

(56) References Cited

U.S. PATENT DOCUMENTS

| | | | | |
|---|---|---|---|---|
| 2014/0356254 | A1* | 12/2014 | Lee | B01L 3/5021 422/548 |
| 2014/0371048 | A1 | 12/2014 | Ra et al. | |
| 2015/0004080 | A1* | 1/2015 | Hassouneh | B01L 3/508 422/548 |
| 2019/0201888 | A1* | 7/2019 | McIntyre | B01L 3/523 |
| 2020/0171485 | A1 | 6/2020 | Heinrich | |

FOREIGN PATENT DOCUMENTS

| | | | | | |
|---|---|---|---|---|---|
| KR | 20140058032 | A | * | 5/2014 | A61M 1/029 |
| KR | 20140135084 | A | | 11/2014 | |
| KR | 10-2015-0008548 | A | | 1/2015 | |
| KR | 101563512 | B1 | | 10/2015 | |
| KR | 20160006078 | A | | 1/2016 | |
| KR | 101646751 | B1 | * | 8/2016 | A61B 5/15 |
| KR | 10-2017-0010575 | A | | 2/2017 | |
| KR | 101930290 | B1 | * | 12/2018 | A61M 1/029 |
| KR | 20190059019 | A | | 5/2019 | |
| KR | 102339809 | B1 | | 12/2021 | |

OTHER PUBLICATIONS

Office Action for IN 202347064911 by Intellectual Property India dated Aug. 28, 2025.
Office Action for CN 202210276126.6 by China National Intellectual Property Administration dated Mar. 13, 2026.

* cited by examiner

BIO KIT FOR EXTRACTING BODILY FLUIDS CONTAINING STEM CELLS

CROSS-REFERENCE TO RELATED APPLICATION

This application claims priority to and the benefit of Korean Patent Application No. 10-2021-0041242, filed on Mar. 30, 2021, the disclosure of which is incorporated herein by reference in its entirety.

TECHNICAL FIELD

The present invention relates to a kit for extracting a buffy coat separated into a layer by centrifugation of blood to the outside, and more particularly, to a bio kit for extracting bodily fluids containing stem cells that can precisely and conveniently extract and separate a buffy coat that has been centrifuged by a centrifuge and separated into an intermediate layer, by an injection needle for extraction that enters from the side.

BACKGROUND

In general, blood performs functions to transport oxygen received from the lungs to tissue cells, transport carbon dioxide from the tissue to the lungs and release them outward, carry nutrients absorbed from the digestive tract to organs or tissue cells, and transport substances unnecessary to the living body, which are decomposition products of tissues, to the kidneys and excrete them out of the body.

Such blood consists of red blood cells, white blood cells, and platelets, and among them, platelets are mainly present in plasma, and plasma is classified into PRP (Platelet rich plasma) and PPP (Platelet poor plasma).

Among such plasma, PRP, in particular, is used for therapeutic purposes because it plays a role in helping the generation of cells through stimulation of stem cells by being implanted in painful areas, particularly knee anterior, ligaments, muscles, and the like.

Recently, autologous blood cell regeneration procedure (also referred to as platelet rich plasma procedure, hereinafter referred to as "PRP procedure") has been in the spotlight, and this procedure refers to a procedure that heals wounds by extracting PRP from one's own blood and injecting it into the damaged area of the cell tissue to regenerate the cell tissue.

Blood platelets are known to be rich in growth factors, and these platelets are known to proliferate cells, produce collagen, regenerate new blood vessels, and heal wounds in the human body.

That is, human blood contains about 100,000 to 200,000 platelets per microliter, and in order for the PRP procedure to be effective, platelets must be concentrated enough to contain more than 1 million platelets per microliter.

The method of concentrating these platelets uses a method of separating the collected blood into layers using a centrifuge, and when normal blood is separated into layers by a centrifuge, it is separated into layers by component in order of weight according to specific gravity, wherein a red red blood cell layer is formed on the lowermost layer, a deep yellow buffy coat layer made of white blood cells and platelets is formed on the red blood cell layer, and a pale yellow plasma layer made of plasma is formed on the uppermost layer over the buffy coat layer.

The volume ratio of each layer of blood thus separated is, on average, 45% of the red blood cell layer, 1% of the buffy coat layer, and 54% of the plasma layer.

Accordingly, the PRP procedure extracts and uses the platelet-rich buffy coat layer from the blood separated as described above, and the ratio is only 1%.

(Patent Document 1) Korean Patent Registration No. 10-1489461 B1 (2015 Jan. 28)

(Patent Document 2) Korean Patent Registration No. 10-1563512 B1 (2015 Oct. 21)

(Patent Document 3) Korean Patent Registration No. 10-1588754 B1 (2016 Jan. 20)

In Patent Document 1, Patent Document 2, and Patent Document 3, a certain amount of blood, which is the object of centrifugation to extract the buffy coat, was injected through the upper housing, and in the blood separation layer centrifuged into the red blood cell layer, the buffy coat layer and the plasma layer, the lower housing is moved relative to the upper hollow tube so that the buffy coat layer, which is the middle layer, was located on the neck portion with a small inner diameter, and then the buffy coat layer was taken out by using an injection needle for extraction that entered through the upper hollow tube.

However, in a state where the buffy coat layer of the separated blood is placed on the neck portion with a small inner diameter after centrifugation of the blood, in the process of taking out the buffy coat layer having a thin layer thickness by entering a long injection needle for extraction through the partially open area of the upper housing, there was a problem in that the amount of extraction varies depending on the skill level of the operator.

The above information disclosed in this Background section is only for enhancement of understanding of the background of the invention and it may therefore contain information that does not form the prior art that is already known to a person of ordinary skill in the art.

SUMMARY

Technical Problem

The present invention has been made to solve the above-mentioned problems and is directed to providing a bio kit for extracting bodily fluids containing stem cells that can separate and extract a buffy coat separated into an intermediate layer to the outside after centrifugation of blood more conveniently and precisely regardless of the skill of the operator.

The problems of the present invention are not limited to those mentioned above, and other problems not mentioned will be clearly understood by those of ordinary skill in the art from the following description.

Technical Solution

According to an aspect of the present invention, in a kit for extracting a buffy coat separated into a layer after centrifugation of blood in a centrifuge to separate into a red blood cell layer, a buffy coat layer and a plasma layer, provided is a centrifugal buffy coat extraction kit including: an upper cap having an opening/closing member for opening and closing an inlet through which the blood is injected; a main body housing having an open upper end outer surface thereof assembled with the upper cap, having a neck portion of a certain length having an inner diameter smaller than an inner diameter of the open upper end in the middle of the length, and having an inner space in which the blood is filled with a certain amount; an adjustment housing that is coupled to the main body housing to seal the open lower end of the main body housing, and is movably assembled with respect to the main body housing so that the buffy coat layer is positioned on the neck portion; and a side cap fixed to the neck portion by forming a needle hole through which an end of an injection needle for extraction enters and exits in area corresponding to a sealing member to seal an extraction hole formed through the neck portion.

In this case, the opening/closing member may include a first opening/closing member having an external tube body that forms on the inner surface a female threaded portion screwed with a male threaded portion formed on the inlet extending from the upper cap to a predetermined height, and having an inner tube body correspondingly inserted into the inner hole of the inlet; and a second opening/closing member that have a membrane member covering a central hole formed through to communicate with the inner hole of the inner tube body, and that is inserted and placed in a placement portion recessed in the first opening/closing member.

In this case, the membrane member may be made of a plate-shaped filter member that allows gas inside the main body housing to permeate and does not allow the blood inside the main body housing to permeate.

In this case, the inner surface of the side cap may be fixedly coupled by an ultrasonic welding method with the upper end of a hollow extension tube, which extends outward by a predetermined length from the neck portion formed through the extraction hole and on which the sealing member is press-fitted.

In this case, the kit may include a bucket housing coupled to the adjustment housing by forming a guided groove corresponding to a guide groove formed in the longitudinal direction on the lower end outer surface of the adjustment housing on the inner surface in the longitudinal direction.

Advantageous Effects

According to the above configuration, the bio kit for extracting bodily fluids containing stem cells according to the present invention performs the operation of adjusting and positioning the buffy coat layer separated by the centrifugal process in the area of the neck portion corresponding to the side cap by means of precise and delicate rotation of the adjustment housing, thereby capable of easily and precisely separate and extract the buffy coat layer centrifuged into a layer, so it is possible to increase the separation extraction amount and purity for the buffy coat that is separated in a small amount.

In addition, the bio kit for extracting bodily fluids containing stem cells according to the present invention can perform conveniently and precisely the process of separating and extracting only the buffy coat layer of blood that is centrifuged in a centrifuge regardless of the skill of the operator, thereby capable of improving convenience of use and increasing customer satisfaction.

Advantageous effects of the present invention are not limited to the above-described effects and should be understood to include all effects that can be inferred from the configuration of the invention described in the detailed description or claims of the present invention.

BRIEF DESCRIPTION OF THE DRAWINGS

The above and other aspects, features, and advantages of the present invention will become more apparent to those of ordinary skill in the art by describing embodiments thereof in detail with reference to the accompanying drawings, in which.

DETAILED DESCRIPTION OF THE EMBODIMENTS

Figure 1:
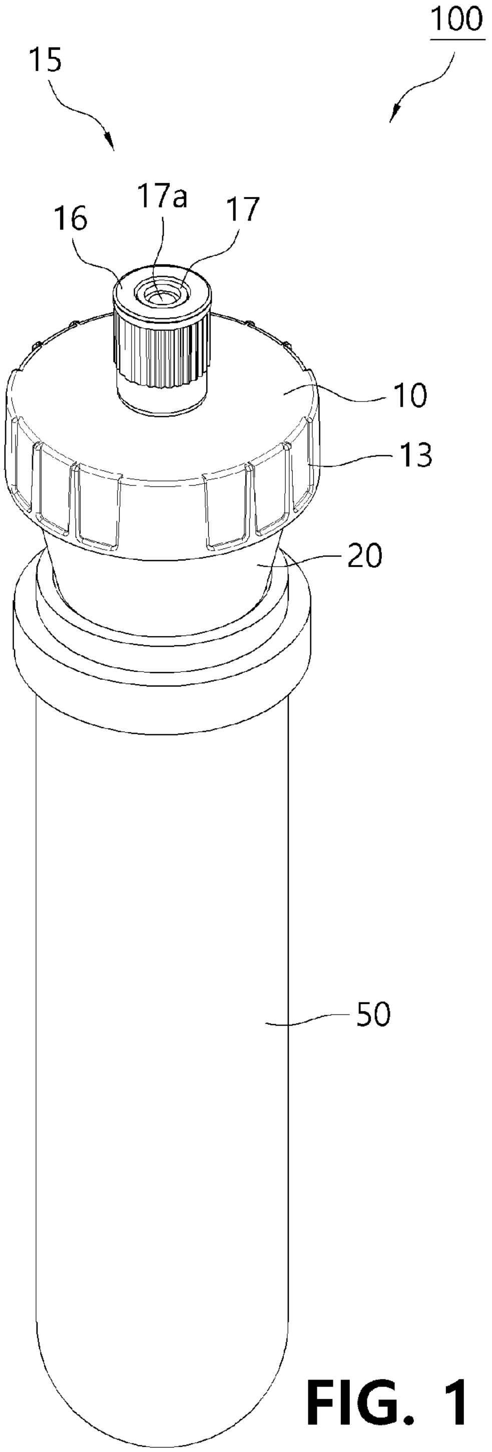
FIG. 1 is an overall perspective view illustrating a state in which a bucket is combined in a bio kit for extracting bodily fluids containing stem cells according to an exemplary embodiment of the present invention.
Figure 2:
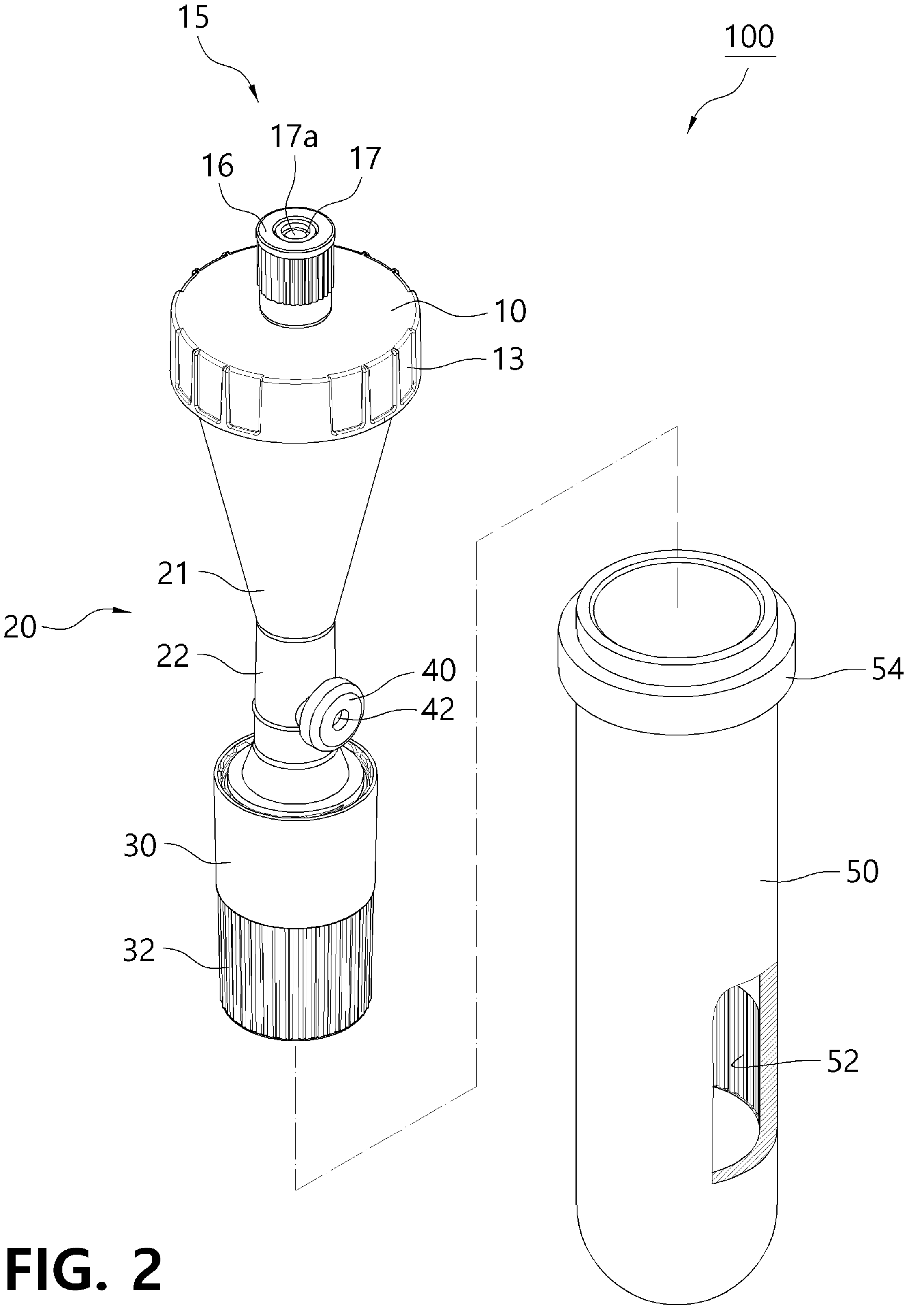
FIG. 2 is an overall perspective view illustrating a state in which a bucket is removed from a bio kit for extracting bodily fluids containing stem cells according to an exemplary embodiment of the present invention.

Hereinafter, exemplary embodiments of the present invention will be described in detail so that those of ordinary skill in the art can readily implement the present invention with reference to the accompanying drawings. The present invention may be embodied in many different forms and is not limited to the embodiments set forth herein. In the drawings, parts unrelated to the description are omitted for clarity. Throughout the specification, like reference numerals denote like elements.

Terms and words used in the present specification and claims should not be construed as limited to their usual or dictionary definition, and they should be interpreted as a meaning and concept consistent with the technical idea of the present invention based on the principle that inventors may appropriately define the terms and concept in order to describe their own invention in the best way.

Accordingly, the embodiments described in the present specification and the configurations shown in the drawings correspond to preferred embodiments of the present invention, and do not represent all the technical spirit of the present invention, so the configurations may have various examples of equivalent and modification that can replace them at the time of filing the present invention.

It is understood that the terms “comprise” or “have” when used in this specification, are intended to describe the presence of stated features, integers, steps, operations, elements, components and/or a combination thereof but not preclude the possibility of the presence or addition of one or more other features, integers, steps, operations, elements, components, or a combination thereof.

The presence of an element in/on "front", "rear", "upper or above or top" or "lower or below or bottom" of another element includes not only being disposed in/on "front", "rear", "upper or above or top" or "lower or below or bottom" directly in contact with other elements, but also cases in which another element being disposed in the middle, unless otherwise specified. In addition, unless otherwise specified, that an element is "connected" to another element includes not only direct connection to each other but also indirect connection to each other.

Hereinafter, a bio kit for extracting bodily fluids containing stem cells according to an embodiment of the present invention will be described in detail with reference to the drawings.

As shown in FIGS. 1, 2, 3 and 4, the bio kit 100 for extracting bodily fluids containing stem cells according to a preferred embodiment of the present invention may have a space in which the blood extracted from the body is accommodated, and may include an upper cap 10, a main body housing 20, an adjustment housing 30, and a side cap 40 so that from the blood centrifuged into a red blood cell layer S1, a buffy coat layer S2 and a plasma layer S3 in a centrifuge, only a buffy coat centrifuged and separated into an intermediate layer can be selectively separated and extracted.

Figure 3:
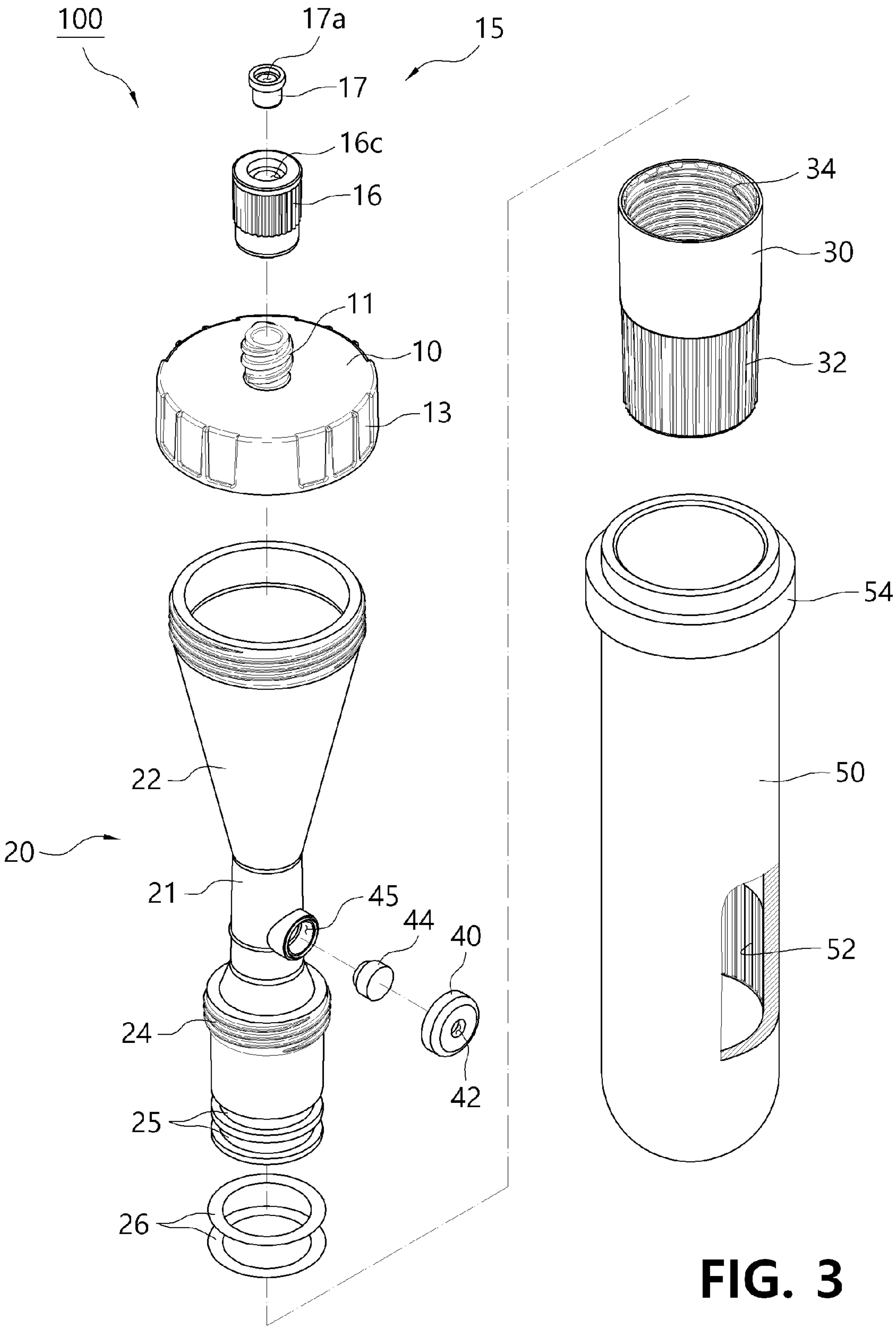
FIG. 3 is an exploded perspective view illustrating a bio kit for extracting bodily fluids containing stem cells according to an exemplary embodiment of the present invention.
Figure 4:
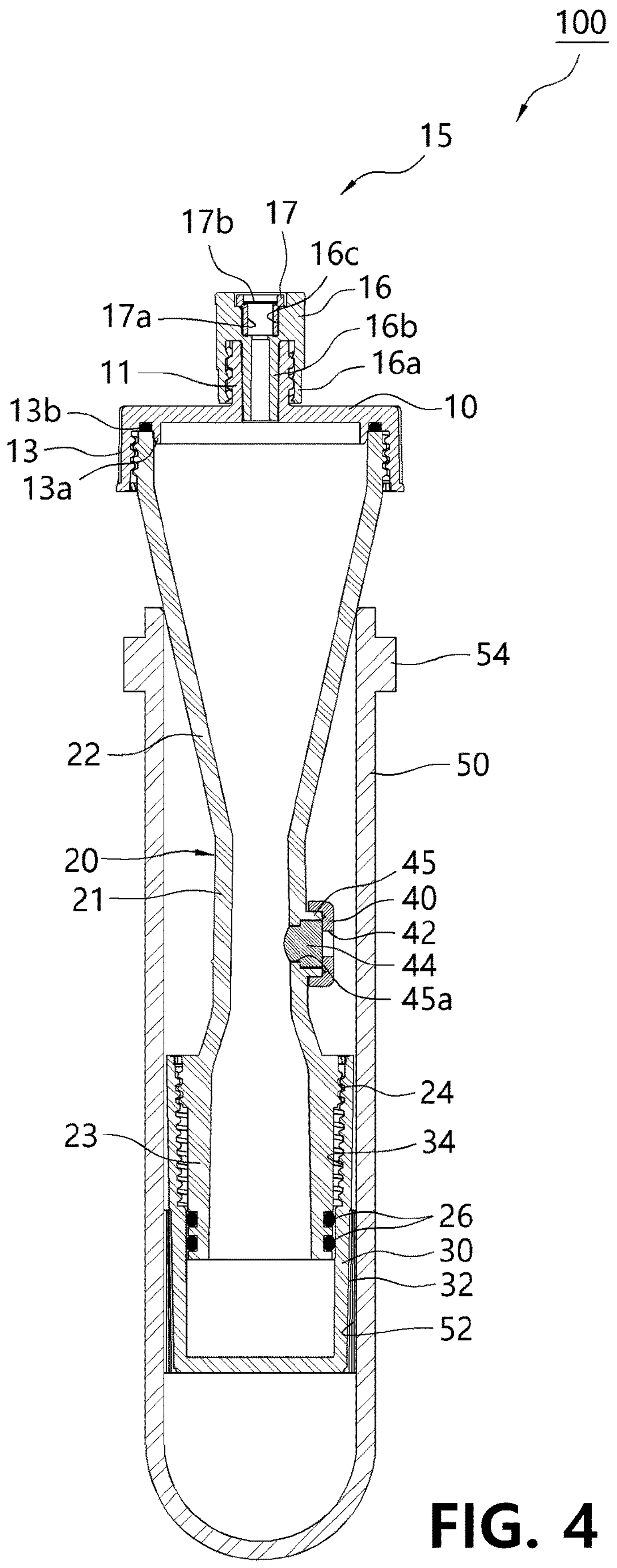
FIG. 4 is a longitudinal cross-sectional view illustrating a bio kit for extracting bodily fluids containing stem cells according to an exemplary embodiment of the present invention.
Figure 5:
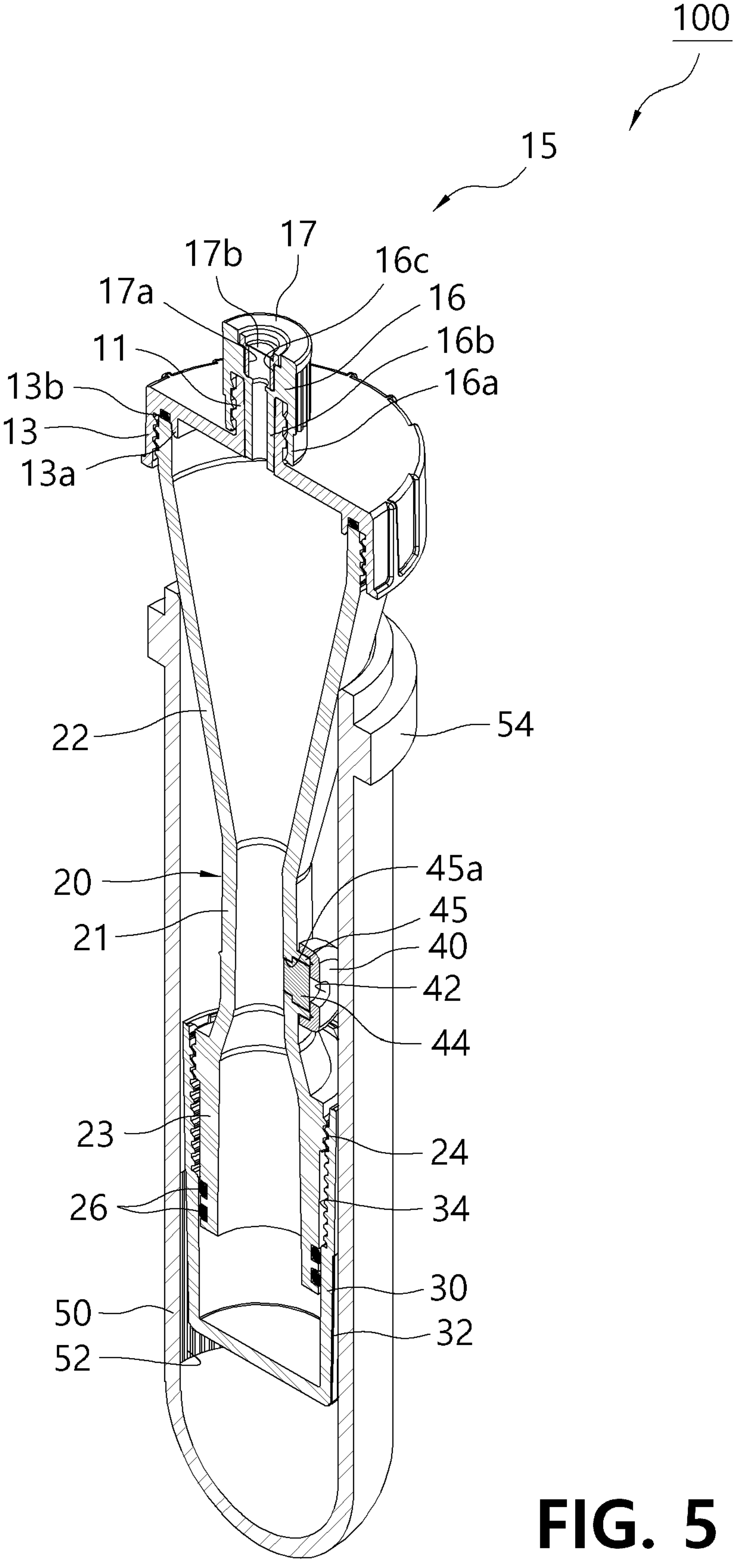
FIG. 5 is a cross-sectional perspective view illustrating a bio kit for extracting bodily fluids containing stem cells according to an exemplary embodiment of the present invention.

As shown in FIGS. 3, 4 and 5, the upper cap 10 is a cap member detachably coupled to the open upper end of the main body housing 20, the upper cap having an inlet 11 through which blood to be centrifuged in the centrifuge is injected through the center of the body and including an opening/closing member 15 for selectively opening and closing the inlet 11.

An outer rim of the upper cap 10 may have an outer extension 13 formed on an inner surface of a female threaded portion screwed with a male threaded portion formed on an outer surface of the open upper end of the main body housing 20, and an inner extension 13*a* that is press-fitted to the inner surface of the open upper end of the main body housing 20 may be provided inside the outer extension.

Between the outer extension 13 and the inner extension 13*a*, a ring-shaped sealing member 13*b* may be provided for sealing the coupling portion between the upper cap 10 and the main body housing 20 to prevent blood from flowing out during centrifugation when the upper cap and the main body housing are coupled.

Figure 6A:
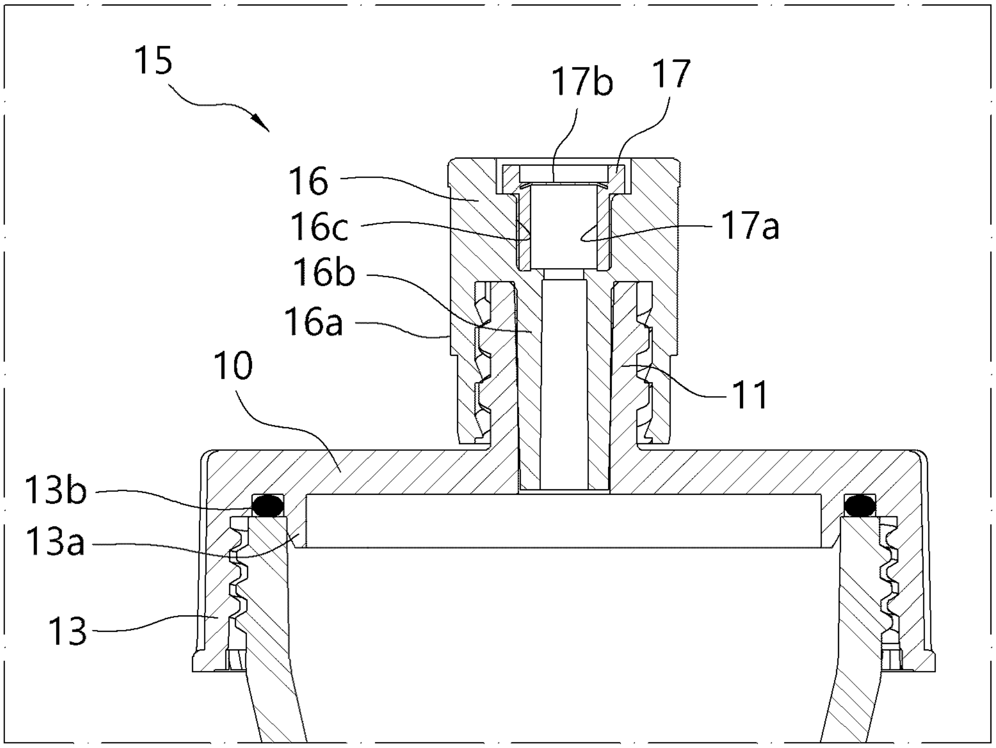
FIG. 6A is a detailed cross-sectional view illustrating a coupling state of an opening/closing member and an upper cap in a bio kit for extracting bodily fluids containing stem cells according to an exemplary embodiment of the present invention.

And, as shown in FIG. 6A, the upper cap 10 may include an opening/closing member 15 that selectively opens or closes the inlet 11 to open and close an injection passage through which blood to be centrifuged is injected.

The opening/closing member 15 may include a first opening/closing member 16 having an external tube body 16*a* that forms on the inner surface a female threaded portion screwed with a male threaded portion formed on the outer surface of the inlet 11 extending from the upper surface of the upper cap 10 to a predetermined height, and having an inner tube body 16*b* correspondingly inserted into the inner hole of the inlet 11 so that the outer surface is in close contact with the inner hole; and may include a second opening/closing member 17 that have a membrane member 17*b* covering and closing a central hole 17*a* formed through to communicate with the inner hole of the inner tube body, and that is inserted, placed and fixed in a placement portion 16*c* recessed in the upper surface of the first opening/closing member.

In this case, the membrane member 17*b* may be made of a plate-shaped filter member that allows gas such as air to permeate and liquid such as blood not to permeate, thereby blocking the external outflow of blood injected into the inner space of the main body housing when the blood is centrifuged, while discharging the air remaining inside the main body housing to the outside to prevent the internal pressure of the main body housing from rising more than necessary.

Figure 7A:
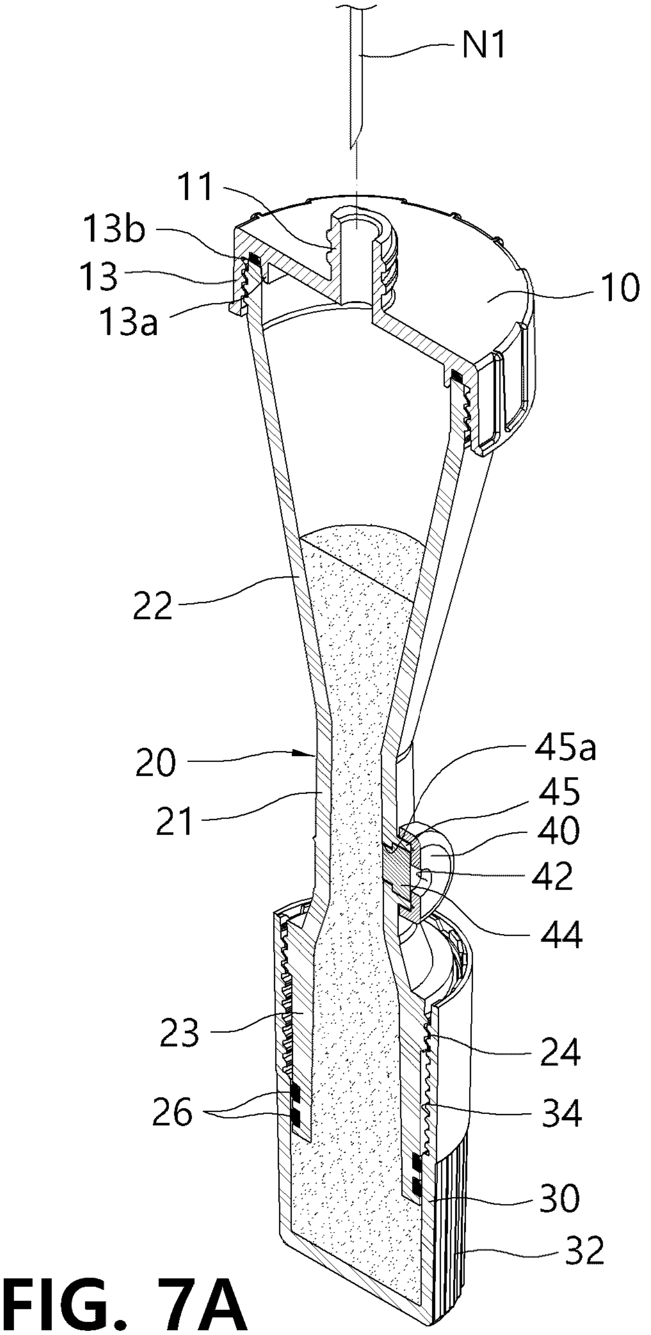
FIGS. 7A, 7B, 7C and 7D are usage state diagrams illustrating a process of injecting blood, centrifuging the blood, and then separating a buffy coat separated into a layer, in a bio kit for extracting bodily fluids containing stem cells according to an exemplary embodiment of the present invention.

Accordingly, as shown in FIG. 7A, the inlet 11 of the upper cap 10 is opened by the separation and release of the opening/closing member 15 coupled in a screw manner, and thus a certain amount of blood extracted from the human body by the injection needle for injection N1 is injected and filled into the inner space of the main body housing 20 through the opened inlet 11, and after the blood injection is completed, the inlet 11 opened by the opening/closing member 15 is blocked and sealed before the centrifugation process by the centrifuge.

As shown in FIGS. 3, 4 and 5, the main body housing 20 is detachably assembled with the upper cap 10 and the open upper end outer surface, and is a hollow member having an internal space of a certain size that is filled with a certain amount of blood to be separated into the red blood cell layer S1, the buffy coat layer S2 and the plasma layer S3.

The main body housing 20 may have a neck portion 21 having an inner diameter smaller than the inner diameter of the open upper end coupled to the upper cap 10 in the middle of the length, and have a side cap 40 coupled to the neck portion 21 so that the buffy coat layer S2 separated into a layer can be selectively separated and extracted.

The main body housing 20 may include an upper hollow tube 22 having a cross-section in which the inner diameter gradually increases from the upper end of the hollow cylindrical neck portion 21 having a constant inner diameter toward the open upper end coupled to the upper cap 10 to form an inclined inner surface, and may include a lower hollow tube 23 extending a certain length downward from the lower end of the neck portion 21 and having a male threaded portion for adjustment 24 formed on the outer surface so as to be screwed with the adjustment housing 30.

The lower hollow tube 23 preferably has an O-ring groove 25 in which at least one O-ring member 26 is disposed to be closed while sliding in contact with the inner surface of the adjustment housing 30 on the lower end outer surface corresponding to the inner surface of the adjustment housing.

Figure 7B:
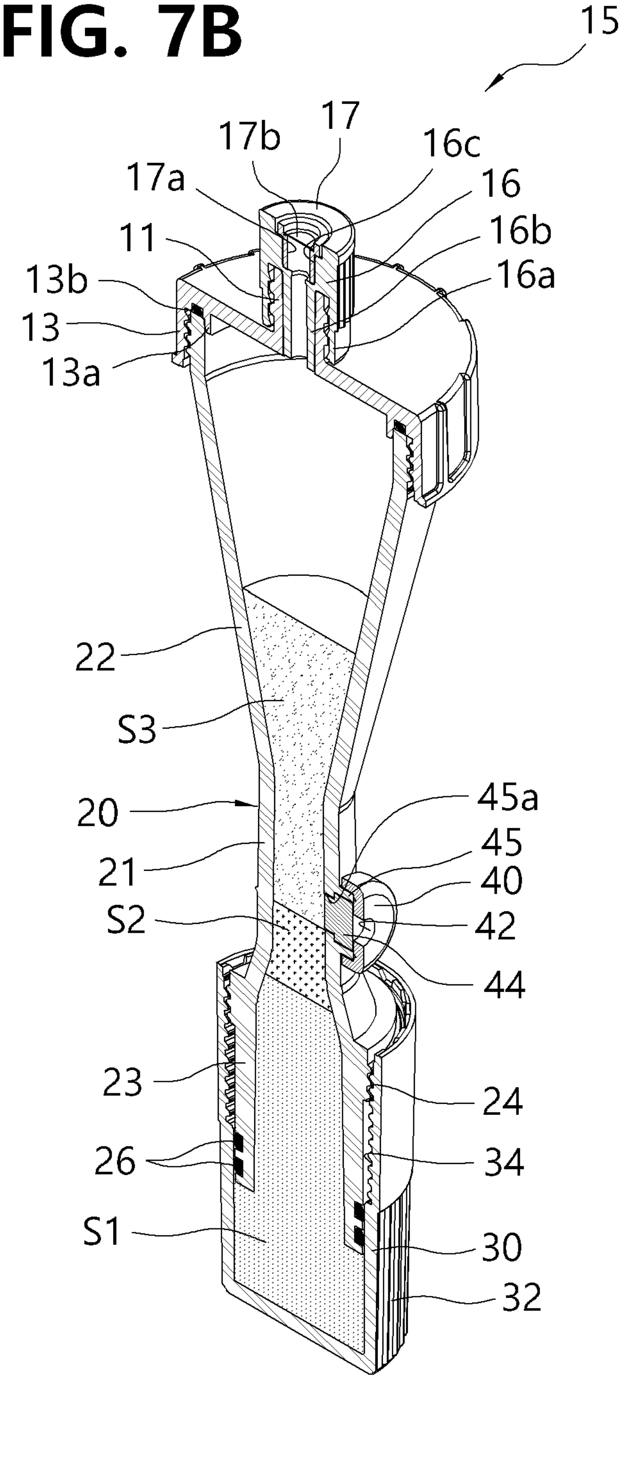

Accordingly, as shown in FIGS. 7A and 7B, the open upper end of the upper hollow tube 22 and the open lower end of the lower hollow tube 23 constituting the main body housing 20 are sealed respectively by the upper cap 10 and the adjustment housing 30, and the inner space of the body housing 20, whose upper and lower ends are sealed, is filled with a certain amount of blood, which is a centrifugal separation object injected by an injection needle for injection, and the open inlet 11 is sealed by an opening/closing member.

As shown in FIGS. 3, 4 and 5, the adjustment housing 30 may be formed in a hollow cylindrical shape with an open upper portion and a closed bottom surface so as to be coupled and closed with the open lower end of the main body housing.

The adjustment housing 30 may be assembled to be movable up and down by having a female threaded portion for adjustment 34 on the upper outer surface so that it can be screwed with the male threaded portion for adjustment 24 formed on the lower hollow tube 23 of the main body housing 20 so that after centrifugation of blood, the buffy coat layer S2 separated into a layer can be properly positioned in the neck portion 21 corresponding to the side cap 40.

Figure 7C:
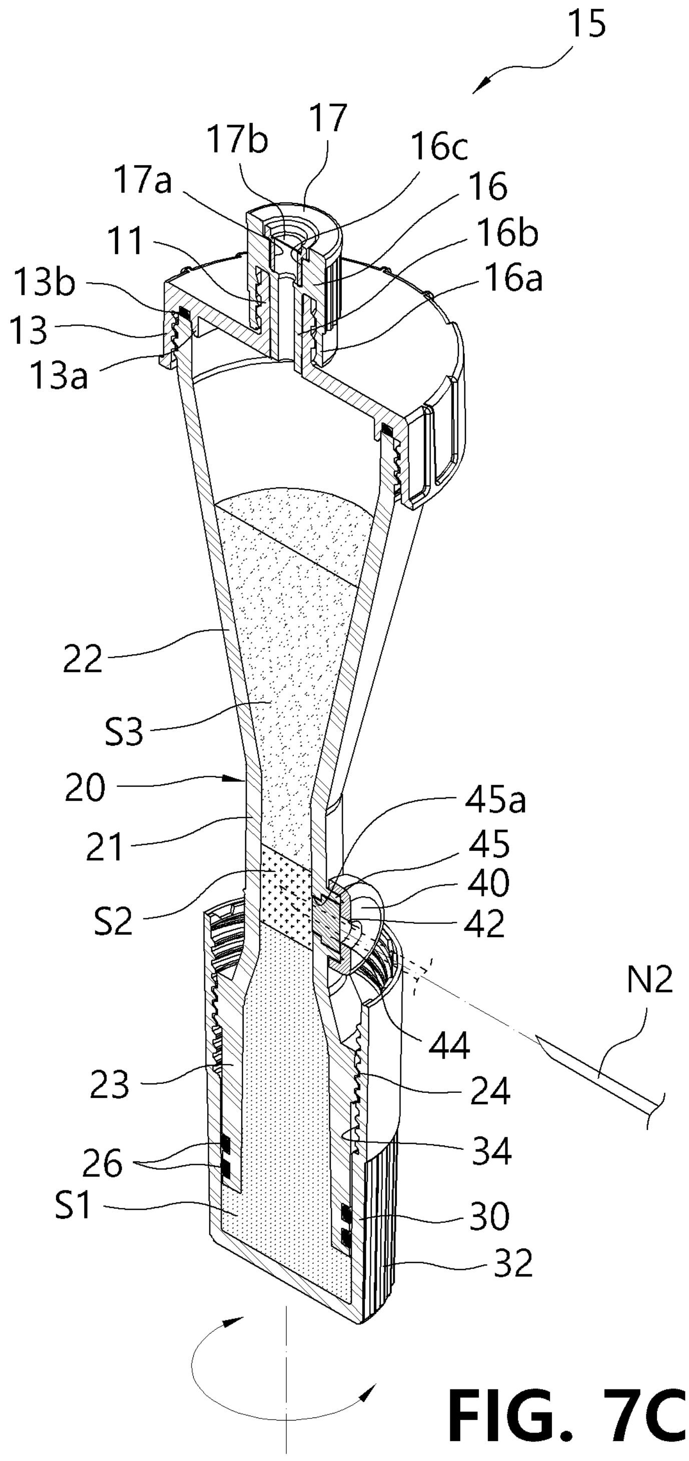

Accordingly, as shown in FIG. 7C, when the adjustment housing 30 is rotated in a forward or reverse direction with respect to the main body housing 20 in a screw manner, the adjustment housing 30 is relatively moved in the longitudinal and up and down direction of the main body housing in proportion to the amount of rotation while reducing or expanding the volume of the centrifugal separation space formed by the upper cap 10, the main body housing 20 and the adjustment housing 30, and thus may adjust the buffy coat layer S2 separated into the middle layer to correspond to the side cap 40 provided in the neck portion 21 having a constant inner diameter to be properly positioned.

As shown in FIGS. 3, 4 and 5, the side cap 40 is a cap member fixed to the neck portion 21 by forming a needle hole 42 of a certain size through the center of the body such that the end of the injection needle for extraction N2 enters and exits the area corresponding to a sealing member 44 press-fitted to seal an extraction hole 45*a* formed through the outer surface of the neck portion of the main body housing.

Figure 6B:
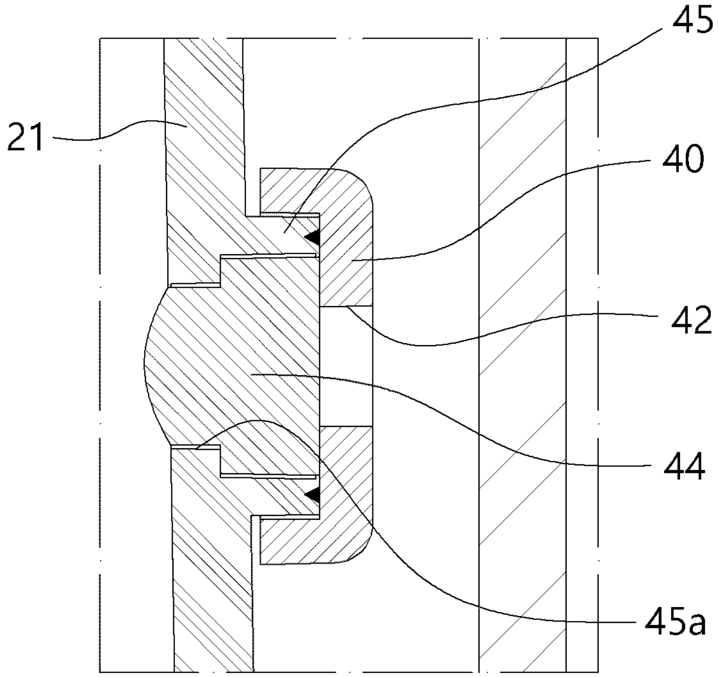
FIG. 6B is a detailed cross-sectional view illustrating a coupling state of a side cap and a neck portion in a bio kit for extracting bodily fluids containing stem cells according to an exemplary embodiment of the present invention.

As shown in FIG. 6B, the side cap 40 may be fixedly coupled by an ultrasonic welding method by the inner surface thereof being in contact with the upper end of a hollow extension tube 45, which extends outward by a predetermined length from the outer surface of the neck portion 21 formed through the extraction hole and on which the sealing member 44 is press-fitted.

In this case, the sealing member 44 is preferably made of a rubber material so that the injection needle for extraction that enters through the needle hole 42 of the side cap is elastically press-fitted while penetrating into the inside of the neck portion 21 to prevent the outflow of blood.

Accordingly, as the blood separated into the red blood cell layer S1, the buffy coat layer S2 and the plasma layer S3 injected into the inner space of the main body housing 20 after centrifugation in the centrifuge is adjusted up and down by the rotation operation of the adjustment housing, the buffy coat layer S2, which is an intermediate layer, corresponds to the side cap 40 of the neck portion 21 in one-to-one correspondence with each other.

In this state, as shown in FIG. 7C, when the operator inserts the end of the injection needle for extraction N2 to the needle hole 42 of the side cap 40 correspondingly, since the end of the injection needle for extraction penetrating the sealing member 44 exposed to the outside through the needle hole 42 is located in the buffy coat layer that is position-adjusted in the neck portion, only the buffy coat layer, which has a very small volume compared to the red blood cell layer and the plasma layer that are separated into the upper and lower layers, can be precisely separated and extracted to the outside.

Then, after the separation extraction of the buffy coat layer S2 using the injection needle for extraction N2 is completed, even though the injection needle for extraction is pulled out and separated from the sealing member 44, the area through which the injection needle for extraction has penetrated is restored to its original state and resealed by the elastic restoring force of the sealing member 44 made of rubber material, thus following separation and extraction of the buffy coat layer S2, the red blood cell layer S1 or the plasma layer S3 remaining in the main body housing 20 can be prevented from flowing out.

Meanwhile, as shown in FIGS. 1, 2, 3, 4 and 5, a bucket housing 50 coupled to the adjustment housing 30 by forming a guided groove 52 corresponding to the guide groove 32 formed in the longitudinal direction on the lower end outer surface of the adjustment housing 30 on the inner surface in the longitudinal direction may be included.

The bucket housing 50 may be coupled to the adjustment housing so that, when the main body housing is accommodated inside, the open upper inner rim of the bucket housing is in contact with the outer surface of the upper housing of the main body housing.

The bucket housing 50 may have a ring-shaped latching jaw 54 formed protruding to be hooked and connected to a latching groove of a rotating body rotating at high speed by the rotational driving force of a motor member in a centrifuge.

Accordingly, after a kit 100 in which blood to be centrifuged is injected into the main body housing is inserted into the bucket housing correspondingly, in the centrifugation process, as the rotating body of the centrifuge rotates at high speed, the kit is rotated at high speed while accommodating the kit inside so that the blood is centrifuged.

Figure 7D:
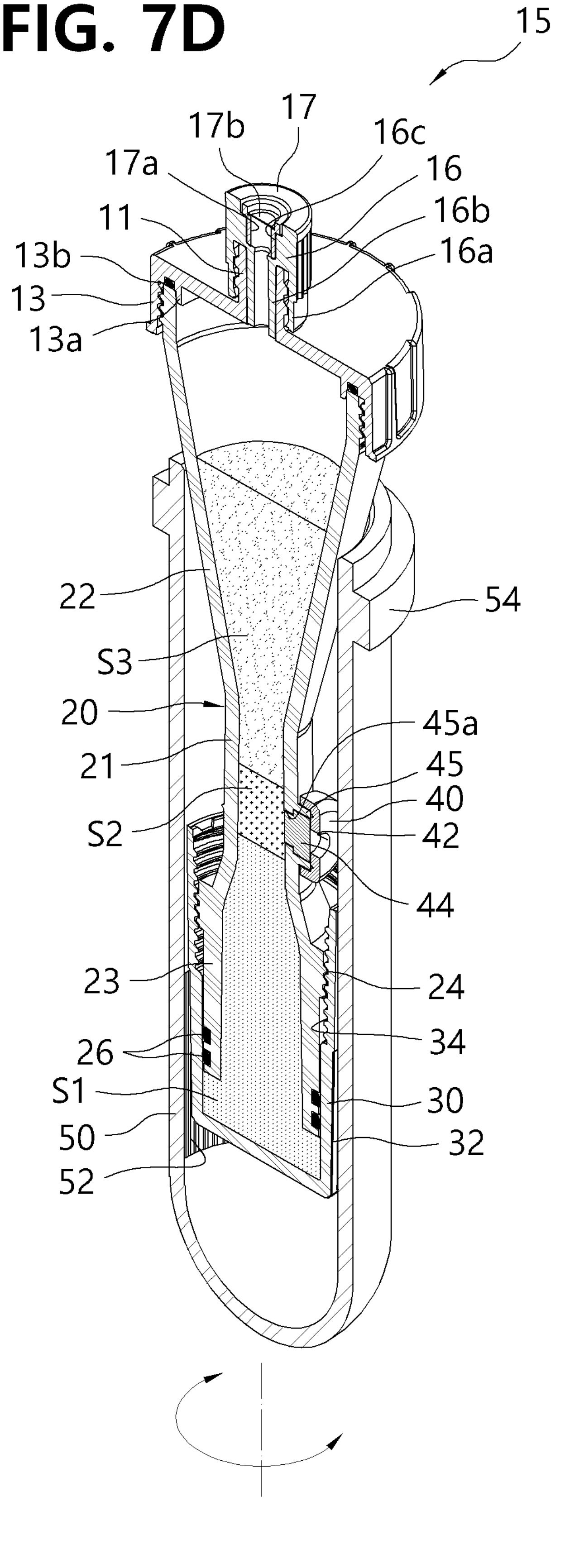

And, as shown in FIG. 7D, it can be adjusted so that the buffy coat layer separated into a layer after centrifugation can be positioned properly on the side cap of the neck portion using the bucket housing coupled with the adjustment housing.

That is, when the operator rotates the body housing 20 in a screw method with respect to the bucket housing in the forward or reverse direction while holding the bucket housing, as the guided groove 52 of the bucket housing 50 and the guide groove 32 are assembled and the adjustment housing 30 disposed inside the bucket housing is relatively moved in the longitudinal direction in proportion to the amount of rotation, the adjustment housing can reduce or expand the volume of the centrifugal separation space formed by the upper cap 10, the main body housing 20 and the adjustment housing 30, and thus can adjust and position properly the buffy coat layer S2 separated into an intermediate layer to correspond to the side cap 40 provided in the neck portion 21 having a constant inner diameter.

Although exemplary embodiments of the present invention have been described, the spirit of the present invention is not limited to the embodiments set forth herein. Those of ordinary skill in the art who understand the spirit of the present invention may easily propose other embodiments through supplement, change, removal, addition, etc. of elements within the same spirit, but the embodiments will be also within the scope of the present invention.

DESCRIPTION OF SYMBOLS

10: upper cap
11: inlet 15: opening/closing member
16: first opening/closing member 17: second opening/closing member
20: main body housing
21: neck portion 22: upper hollow tube
23: lower hollow tube 24: male threaded portion for adjustment
30: adjustment housing
32: guide groove 34: female threaded portion for adjustment
40: side cap
42: needle hole 44: sealing member
50: bucket housing
S1: red blood cell layer S2: buffy coat layer
S3: plasma layer N1: injection needle for injection
N2: injection needle for extraction

What is claimed is:

1. A bio kit for extracting bodily fluids containing stem cells in the bio kit for extracting a buffy coat separated into a layer, after centrifugation of blood in a centrifuge to separate into a red blood cell layer, a buffy coat layer and a plasma layer and comprising:

an upper cap having an opening/closing member for opening and closing an inlet through which the blood is injected;

a main body housing having an open upper end outer surface thereof assembled with the upper cap, having a neck portion of a certain length having an inner diameter smaller than an inner diameter of the open upper end in the middle of the length, and having an inner space in which the blood is filled with a certain amount;

an adjustment housing that is coupled to the main body housing to seal the open lower end of the main body housing, and is movably assembled with respect to the main body housing so that the buffy coat layer is positioned on the neck portion; and a side cap fixed to the neck portion by forming a needle hole through which an end of an injection needle for extraction enters and exits in area corresponding to a sealing member to seal an extraction hole formed through the neck portion;

wherein the opening/closing member comprises a first opening/closing member having an external tube body that forms on an inner surface a female threaded portion screwed with a male threaded portion formed on an outer surface of the inlet extending from the upper cap to a predetermined height, and wherein the first opening/closing member comprises an inner tube body correspondingly inserted into an inner hole of the inlet so that an outer surface of the inner tube body is in close contact with the inner hole of the inlet;

a second opening/closing member that has a membrane member covering a central hole formed through to communicate with an inner hole of the inner tube body of the first opening/closing member, and wherein the second opening/closing member is inserted and placed in a placement portion recessed in an upper surface of the first opening/closing member;

wherein the membrane member is provided as a plate-shaped filter member that allows gas inside the main body housing to permeate and does not allow the blood inside the main body housing to permeate;

wherein the main body housing includes an upper hollow tube having a cross-section in which the inner diameter gradually increases from the upper end of the hollow cylindrical neck portion toward the open upper end that is coupled to the upper cap to form an inclined inner surface, and a lower hollow tube extending a certain length downward from the lower end of the neck portion and having a male threaded portion for adjustment formed on the outer surface so as to be screwed with adjustment housing; and wherein the inner surface of the side cap is fixedly coupled by an ultrasonic welding method with the upper end of a hollow extension tube, which extends outward by a predetermined length from the neck portion formed through the extraction hole and on which the sealing member is press-fitted.

2. The bio kit for extracting bodily fluids containing stem cells of claim 1, further comprising a bucket housing coupled to the adjustment housing by forming a guided groove corresponding to a guide groove formed in the longitudinal direction on the lower end outer surface of the adjustment housing on the inner surface in the longitudinal direction.

* * * * *